(12) United States Patent (10) Patent No.: US 8,663,171 B2
Tambourgi et al. (45) Date of Patent: Mar. 4, 2014

(54) MEDICAL-USE BANDAGE

(75) Inventors: Christina Tambourgi, Oullins (FR); Pascal Bernard, Uccle (BE); Jean Michel Goby, Sennecey-les-Dijon (FR)

(73) Assignee: Fresenius Medical Care Deutshland GmbH, Bad Homburg (DE)

( * ) Notice: Subject to any disclaimer, the term of this patent is extended or adjusted under 35 U.S.C. 154(b) by 780 days.

(21) Appl. No.: 12/300,410

(22) PCT Filed: Aug. 30, 2006

(86) PCT No.: PCT/IB2006/002375
§ 371 (c)(1),
(2), (4) Date: May 1, 2009

(87) PCT Pub. No.: WO2007/132288
PCT Pub. Date: Nov. 22, 2007

(65) Prior Publication Data
US 2010/0016802 A1 Jan. 21, 2010

(30) Foreign Application Priority Data
May 12, 2006 (FR) ..................................... 06 04221

(51) Int. Cl.
*A61M 5/32* (2006.01)
(52) U.S. Cl.
USPC .......................................... 604/180; 604/174
(58) Field of Classification Search
USPC ........................... 604/174, 175, 178, 179, 180
See application file for complete search history.

(56) References Cited

U.S. PATENT DOCUMENTS

| 1,570,181 | A | 1/1926 | Owens |
| 1,601,735 | A | 10/1926 | Harris |
| 3,018,881 | A | 1/1962 | Wall |
| 3,285,245 | A | 11/1966 | Eldredge et al. |
| 3,645,835 | A | 2/1972 | Hodgson |
| 3,765,421 | A | 10/1973 | Poprik |
| 3,902,496 | A | 9/1975 | Eakin |
| 4,112,177 | A | 9/1978 | Salditt et al. |
| 4,239,041 | A | 12/1980 | Popovich et al. |
| 4,346,700 | A | 8/1982 | Dunshee et al. |
| 4,366,814 | A | 1/1983 | Riedel |
| 4,578,062 | A | 3/1986 | Schneider |
| 4,582,508 | A | 4/1986 | Pavelka |

(Continued)

FOREIGN PATENT DOCUMENTS

| DE | 39 00 004 A1 | 7/1989 |
| DE | 297 08 126 U1 | 7/1997 |

(Continued)

*Primary Examiner* — Emily Schmidt
(74) *Attorney, Agent, or Firm* — Jacobson Holman PLLC

(57) ABSTRACT

A medical use bandage is configured to immobilize, and to facilitate the use of, a tube implanted in a body. The implanted tube defines a body exit site, and a part of the tube projects from the body. The bandage includes a base support having a lower face for application to the skin and an upper face, a first bandage fixing portion for fixing the exit site, including on the lower face of the base support an adhesive fixing part to be adhered at least partly around the exit site to the skin and to a proximal portion of the projecting part of the tube, and a second bandage fixing portion for engaging the distal portion of the projecting part of the tube in a defined shape and in a sliding manner. The second bandage fixing portion is at least partly a part of the upper face of the support.

26 Claims, 5 Drawing Sheets

(56) References Cited

U.S. PATENT DOCUMENTS

| | | | |
|---|---|---|---|
| 4,662,873 A * | 5/1987 | Lash et al. | 604/179 |
| 4,743,232 A | 5/1988 | Kruger | |
| 4,837,062 A | 6/1989 | Dunshee et al. | |
| 4,955,867 A | 9/1990 | Endo | |
| 4,967,740 A | 11/1990 | Riedel | |
| 5,048,122 A | 9/1991 | Prieur | |
| 5,230,350 A | 7/1993 | Fentress | |
| 5,230,701 A | 7/1993 | Meyer et al. | |
| 5,344,415 A | 9/1994 | DeBusk et al. | |
| 5,369,155 A | 11/1994 | Asmus | |
| 5,382,466 A | 1/1995 | Ingham | |
| 5,384,174 A * | 1/1995 | Ward et al. | 428/41.5 |
| 5,406,267 A | 4/1995 | Curtis | |
| 5,425,719 A | 6/1995 | Lessing, Jr. | |
| 5,456,659 A | 10/1995 | Gildersleeve et al. | |
| 5,468,229 A | 11/1995 | Chandler | |
| 5,496,282 A | 3/1996 | Militzer et al. | |
| 5,531,667 A | 7/1996 | Webb et al. | |
| 5,669,884 A | 9/1997 | Bennes et al. | |
| 5,688,248 A | 11/1997 | Lessing, Jr. | |
| 5,707,348 A | 1/1998 | Krogh | |
| 5,749,843 A | 5/1998 | Miller | |
| 5,776,106 A | 7/1998 | Matyas | |
| 5,840,052 A | 11/1998 | Johns | |
| 5,885,254 A | 3/1999 | Matyas | |
| 5,914,282 A | 6/1999 | Dunshee et al. | |
| 5,939,339 A | 8/1999 | Delmore et al. | |
| 6,004,253 A | 12/1999 | Riedel et al. | |
| 6,027,465 A | 2/2000 | Scholz et al. | |
| 6,126,639 A | 10/2000 | Sutherland et al. | |
| 6,206,854 B1 | 3/2001 | Weaver | |
| 6,267,115 B1 | 7/2001 | Marshel | |
| 6,432,074 B1 | 8/2002 | Ager et al. | |
| 6,436,074 B1 | 8/2002 | Lee | |
| 6,544,232 B1 | 4/2003 | McDaniel | |
| 6,649,804 B2 | 11/2003 | Eakin | |
| 6,706,940 B2 | 3/2004 | Worthley | |
| 6,736,797 B1 | 5/2004 | Larsen et al. | |
| 6,797,855 B2 | 9/2004 | Worthley | |
| 6,840,922 B2 | 1/2005 | Nielsen et al. | |
| 2002/0091347 A1 | 7/2002 | Eakin | |
| 2003/0097086 A1 | 5/2003 | Gura | |
| 2004/0204685 A1 * | 10/2004 | Wright et al. | 604/174 |
| 2005/0020995 A1 | 1/2005 | Shaw | |
| 2005/0028818 A1 | 2/2005 | Svendsen | |
| 2005/0107746 A1 | 5/2005 | Pajunk et al. | |
| 2007/0049859 A1 * | 3/2007 | Propp | 602/58 |
| 2007/0060892 A1 * | 3/2007 | Propp | 604/180 |
| 2007/0106222 A1 * | 5/2007 | Bennett | 604/174 |

FOREIGN PATENT DOCUMENTS

| | | |
|---|---|---|
| DE | 196 03 532 A1 | 8/1997 |
| DE | 199 53 062 A1 | 5/2000 |
| DE | 101 07 189 A1 | 8/2001 |
| EP | 0 057 988 B1 | 8/1982 |
| EP | 0 094 222 B1 | 11/1983 |
| EP | 0 136 021 A2 | 4/1985 |
| EP | 0 147 119 B1 | 7/1985 |
| EP | 0 168 174 A1 | 1/1986 |
| EP | 0 122 085 B1 | 6/1987 |
| EP | 0 249 461 B1 | 12/1987 |
| EP | 0 254 493 A1 | 1/1988 |
| EP | 0 284 219 A2 | 9/1988 |
| EP | 0 319 163 A2 | 6/1989 |
| EP | 0 326 285 A2 | 8/1989 |
| EP | 0 341 875 A2 | 11/1989 |
| EP | 0 343 807 A2 | 11/1989 |
| EP | 0 375 211 B1 | 6/1990 |
| EP | 0 494 083 B1 | 7/1992 |
| EP | 0 507 459 B1 | 10/1992 |
| EP | 0 569 565 B1 | 11/1993 |
| EP | 0 619 105 A1 | 10/1994 |
| EP | 0 639 963 B1 | 3/1995 |
| EP | 0 671 182 A1 | 9/1995 |
| EP | 0 688 845 A1 | 12/1995 |
| EP | 0 726 754 A1 | 8/1996 |
| EP | 0 727 973 B1 | 8/1996 |
| EP | 0 741 589 B1 | 11/1996 |
| EP | 0 795 357 A1 | 9/1997 |
| EP | 0 807 449 B1 | 11/1997 |
| EP | 0 863 775 A2 | 9/1998 |
| EP | 0 872 621 A1 | 10/1998 |
| EP | 0 874 876 B1 | 11/1998 |
| EP | 0 912 645 B1 | 5/1999 |
| EP | 0 971 661 B1 | 1/2000 |
| EP | 0 984 755 B1 | 3/2000 |
| EP | 1 143 895 A1 | 3/2000 |
| EP | 0 991 439 B1 | 4/2000 |
| EP | 1 004 459 A1 | 5/2000 |
| EP | 1 007 133 B1 | 6/2000 |
| EP | 1 165 717 | 9/2000 |
| EP | 1 113 062 A1 | 7/2001 |
| EP | 1 115 333 B1 | 7/2001 |
| EP | 1 142 974 A1 | 10/2001 |
| EP | 1 267 979 B1 | 1/2003 |
| EP | 1 272 244 B1 | 1/2003 |
| EP | 1 316 596 A1 | 6/2003 |
| EP | 1 424 093 A1 | 6/2004 |
| EP | 1 520 601 A2 | 4/2005 |
| FR | 1 288 390 A | 3/1962 |
| FR | 1 314 185 A | 1/1963 |
| FR | 2 581 545 A3 | 11/1986 |
| FR | 2 610 310 A1 | 8/1988 |
| FR | 2 610 909 A1 | 8/1988 |
| FR | 2 664 609 A1 | 1/1992 |
| FR | 2 759 379 A1 | 8/1998 |
| FR | 2 764 502 A1 | 12/1998 |
| FR | 2 770 221 A1 | 4/1999 |
| FR | 2 780 980 A1 | 1/2000 |
| FR | 2 785 526 A1 | 5/2000 |
| FR | 2 796 769 A1 | 1/2001 |
| FR | 2 805 275 A1 | 8/2001 |
| FR | 2 842 469 A1 | 1/2004 |
| FR | 2 843 120 A1 | 2/2004 |
| GB | 987 933 A | 3/1965 |
| GB | 2 094 154 A | 9/1982 |
| GB | 2 295 766 A | 6/1996 |
| GB | 2 326 100 A | 12/1998 |
| GB | 2 330 542 A | 4/1999 |
| WO | 85/01438 A1 | 4/1985 |
| WO | 87/04919 A1 | 8/1987 |
| WO | 88/07847 A1 | 10/1988 |
| WO | 90/09770 A1 | 9/1990 |
| WO | 91/02539 A1 | 3/1991 |
| WO | 93/00788 A1 | 1/1993 |
| WO | 93/06182 A1 | 4/1993 |
| WO | 94/02090 A1 | 2/1994 |
| WO | 94/03539 A1 | 2/1994 |
| WO | 94/21207 A2 | 9/1994 |
| WO | 95/11647 A1 | 5/1995 |
| WO | 95/12375 A2 | 5/1995 |
| WO | 95/18645 A1 | 7/1995 |
| WO | 95/20929 A1 | 8/1995 |
| WO | 95/26698 A1 | 10/1995 |
| WO | 95/33507 A1 | 12/1995 |
| WO | 97/03707 A1 | 2/1997 |
| WO | 97/06836 A2 | 2/1997 |
| WO | 97/21459 A1 | 6/1997 |
| WO | 97/26306 A1 | 7/1997 |
| WO | 97/38646 A2 | 10/1997 |
| WO | 98/03601 A1 | 1/1998 |
| WO | 98/10823 A1 | 3/1998 |
| WO | 98/15312 A1 | 4/1998 |
| WO | 98/38955 A1 | 9/1998 |
| WO | 98/44879 A1 | 10/1998 |
| WO | 98/47452 A1 | 10/1998 |
| WO | 98/58106 A1 | 12/1998 |
| WO | 99/12581 A2 | 3/1999 |
| WO | 99/27808 A1 | 6/1999 |
| WO | 99/40952 A1 | 8/1999 |
| WO | 00/10540 A1 | 3/2000 |
| WO | 00/16725 A1 | 3/2000 |

(56) References Cited

FOREIGN PATENT DOCUMENTS

| | | |
|---|---|---|
| WO | 00/35501 A1 | 6/2000 |
| WO | 00/50094 A1 | 8/2000 |
| WO | 00/53690 A1 | 9/2000 |
| WO | 01/00115 A2 | 1/2001 |
| WO | 01/13853 A1 | 3/2001 |
| WO | 01/54639 A1 | 8/2001 |
| WO | 01/76673 A1 | 10/2001 |
| WO | 02/12410 A1 | 2/2002 |
| WO | 03/032881 A2 | 4/2003 |
| WO | 03/043677 A2 | 5/2003 |
| WO | 03/068305 A1 | 8/2003 |
| WO | 03/071921 A2 | 9/2003 |
| WO | 03/073970 A1 | 9/2003 |
| WO | 2004/020023 A2 | 3/2004 |
| WO | 2004/020035 A1 | 3/2004 |
| WO | 2004/020036 A2 | 3/2004 |
| WO | 2004/020038 A1 | 3/2004 |
| WO | 2004/047700 A1 | 6/2004 |
| WO | 2004/071556 A1 | 8/2004 |
| WO | 2004/071568 A1 | 8/2004 |
| WO | 2004/075795 A1 | 9/2004 |
| WO | 2004/087240 A1 | 10/2004 |
| WO | 2004/100842 A1 | 11/2004 |
| WO | 2005/039466 A2 | 5/2005 |
| WO | 2005/046959 A1 | 5/2005 |

\* cited by examiner back view back view

MEDICAL-USE BANDAGE

TECHNICAL FIELD OF THE INVENTION

The present invention relates to a medical-use bandage for a tube implanted in a patient, and the process for applying this bandage to the skin of a patient. The s tube is more particularly the tube of a catheter for dialysis, notably peritoneal dialysis.

Dialysis is a way of cleaning the blood when a person's kidneys are no longer able to function. Dialysis takes the place of the kidneys by removing the body's waste products, notably excess water or salt. There are two basic methods of dialysis: haemodialysis and peritoneal dialysis.

In haemodialysis the blood is pumped out of the body to a machine which acts as an artificial kidney and contains a special membrane for filtering the blood and removing waste products. The cleaned blood is then returned via tubes connecting the patient to the machine. The haemodialysis process takes approximately 4 hours and must be carried out three times a week.

In peritoneal dialysis the waste products are filtered out of the blood through the wall of the patient's abdominal cavity. The wall is called the peritoneum and acts as a natural filtration membrane. The waste products are removed by means of a sterile cleaning fluid which is introduced and removed from the abdomen in cycles. A flexible plastic tube known as a catheter is permanently installed surgically in the lower part of the patient's abdomen. One part of this catheter is inserted inside the patient and one part projects outside the patient. The junction between the two parts on the surface of the skin is known as the "exit site". The patient therefore has part of the catheter permanently projecting from his or her body.

During the treatment, the distal end (meaning the end furthest from the patient) of the catheter is connected by an adapter to another tube, the patient extender. A connector at the end of the extender allows communication with the cleaning fluid. The cleaning fluid thus enters the abdomen through the extender and then through the catheter.

Waste products from the blood pass through the peritoneal membrane into the cleaning fluid. Then, when the filtration process is over, the fluid leaves the body through the catheter.

More particularly, peritoneal dialysis employs two different methods in terms of duration and the number of cycles: Automatic Peritoneal Dialysis (APD), done by machine, and Continuous Ambulatory Peritoneal Dialysis (CAPD), which uses gravity.

Continuous Ambulatory Peritoneal Dialysis does not require the use of a dialysis machine. Patients perform the treatment themselves by introducing into their abdomen approximately 2 liters of cleaning fluid into their peritoneal cavity by connecting up via the extender a bag of cleaning fluid which is placed above shoulder level and drained in. Then, when the fluid has been introduced into the patient's peritoneal cavity, an empty bag is connected via the extender at a level below the abdomen. In this way the solution containing the waste products is drained off from the peritoneal cavity into the empty bag. This process is usually performed 4 or 5 times every day. Each of these cycles takes around 30 minutes.

In automatic dialysis, these cycles are programmed by a machine at least several times a night.

One drawback with peritoneal dialysis is the permanent installation of the catheter and extender near the patient's belt.

In the first place, the projecting part of this extender (which can measure between 20 and 30 cm) must be protected and kept in position between cycles to avoid damage or movement of the catheter and its extender. In the second place, during the cycle, the projecting part of the tube may move undesirably as the fluid is passing through it. This can be uncomfortable for the patient and can influence the rate of flow of the fluid, or result in the implanted catheter being moved relative to the body.

In addition, the exit site of the catheter must be carefully monitored because it can be subject to unwanted infections (such as peritonitis).

PRIOR ART

As regards the fixing and protecting of the catheter and extender during non-treatment time, a number of dressings or bandages designed to secure the projecting part of the tube are known. The best-known method is a bandage which is made by the patient or nurse and consists of gauze placed on the exit site and then secured with several strips of adhesive tape.

More sophisticated belts having a bag for receiving the unused tube have been developed. U.S. Pat. No. 6,436,074 discloses a belt for securing the catheter and protecting the exit site during non-treatment time. The belt is doubled over and closed to form a bag to receive the tube. The exit site is protected by sterile gauze in contact with the exit site and applied by a block of foam rubber all the way around it. The device is held in place during non-treatment time by its belt shape which is adjusted to fit the patient's pelvis.

As regards the fixing and protection of the catheter during treatment, several bandages have been produced, mostly bandages for applying to a tube connecting a vascular access of a patient.

One bandage for use during treatment is known from Patent U.S. Pat. No. 5,344,415. This bandage comprises two distinct separate parts: the first part is a dressing with an absorbent material applied to the exit site and surrounded by an adhesive dressing. The second part is a simple, entirely adhesive band. The first part is applied first, followed by the second part which will be applied along the edge of the first part covering the tube. In one edge of the second part is an indentation for receiving the tube. The second part is stuck to the skin in such a way as to cover an edge of the first part and immobilize the tube between the two edges inside the indentation.

A second bandage for use during treatment is known from Patent EP 0 569 565. This is a square adhesive bandage with an area of gauze in its centre designed to be placed over the exit site. The bandage is slit through its thickness from the centre of the gauze to the perimeter of the bandage. The slit makes it possible to position the centre of the bandage over the exit site of the patient and allows the bandage to be stuck all the way around the exit site. Where the vascular access device is a cannula assembly comprising a voluminous assembly body comprising two branches, one for the vascular access tube and the other for the administration of medication, the assembly device is itself attached, in addition to the square bandage, by an entirely adhesive band attached to the bandage enabling the vascular access tube to be held in place by adhesive.

The third intravenous bandage for use during treatment is known from U.S. Pat. No. 5,707,348. It is composed of a first part applied all the way around the exit site by adhesive fixing, and a second part which, in the position of complete usage, will be fixed adhesively to the skin to hold the tube in a chosen direction.

Each proposed type uses adhesive fixing for the first part around the vascular access site and adhesive fixing for the second part in such a way that the two parts keep the tube in position adhesively for the whole time the bandage is being used in a chosen form.

Consequently, in the three described cases of dressings used during treatment, each bandage has a single-use adhesive fixing for the tube. In other words, each bandage is applied adhesively to keep the tube immobile throughout the period of application of the bandage. The tube can only be moved when the bandage is removed after the patient has been treated.

The object of the invention is to provide a bandage that will allow the projecting portion of a tube implanted in a patient to be immobilized in a first position during a treatment involving passage of fluid, and immobilized in a second position during non-treatment when there is no passage of fluid.

One object of the invention is to provide a bandage capable of remaining in place on the skin for several days.

Another object of the invention is to provide permanent protection of the patient's exit site.

A further object is to provide a bandage that will allow easy monitoring of the condition of the exit site for the whole of the time during which the bandage is in position.

Additional objects are to obtain a strong bandage that is impermeable to water and bacteria, is easy and inexpensive to produce, is easy for the user to handle when applying it to his skin, and is easy for the user to handle when detaching it.

The dressing can be used for the tube of a catheter implanted in the peritoneum of a patient undergoing peritoneal dialysis, but can be used for any catheter or implanted medical tube that must be secured in two different positions.

SUMMARY OF THE INVENTION

The invention relates to a medical-use bandage 1 having a lower face designed to be turned to the skin, and on the opposite side an upper face; this bandage being designed to immobilize a tube 100 implanted in a body, the implanted tube 100 defining an exit site from the body 101 and a part of the tube 102 projecting from the body; the bandage 1 comprising:
- a base support 2 having a lower face 21 designed to be applied to the skin and, on the opposite side, an upper face 22,
- first fixing means 3 for fixing the exit site 101, comprising on the lower face 21 of the base support 2 an adhesive fixing part 32 designed to be stuck at least partly around the exit site 101 to the skin and to a proximal portion 102' of the projecting part 102 of the tube; and
- second fixing means 4 for engaging the distal portion 102" of the projecting part 102 of the tube in a defined shape and in a sliding manner, the second fixing means 4 consisting at least partly of a part 43 of the upper face 22 of the support 2.

The invention also relates to a process for applying the bandage according to the invention comprising the following steps:
- applying and fixing adhesively at least in part the first fixing means 3 to the skin and the proximal part of the projecting portion of the tube,
- applying and fixing adhesively at least in part the second fixing means 4 to the skin, and
- forming a loop with the distal portion of the projecting part of the tube and engaging the projecting part of the tube in a sliding manner in the second fixing means and in contact with at least the part 43 of the upper surface 22 of the support 2.

BRIEF DESCRIPTION OF THE DRAWINGS

Other advantages and features of the invention will become apparent on reading the description which follows.

The reader should refer to the accompanying drawings, in which.

DETAILED DESCRIPTION OF THE EMBODIMENTS OF THE INVENTION

Figure 1:
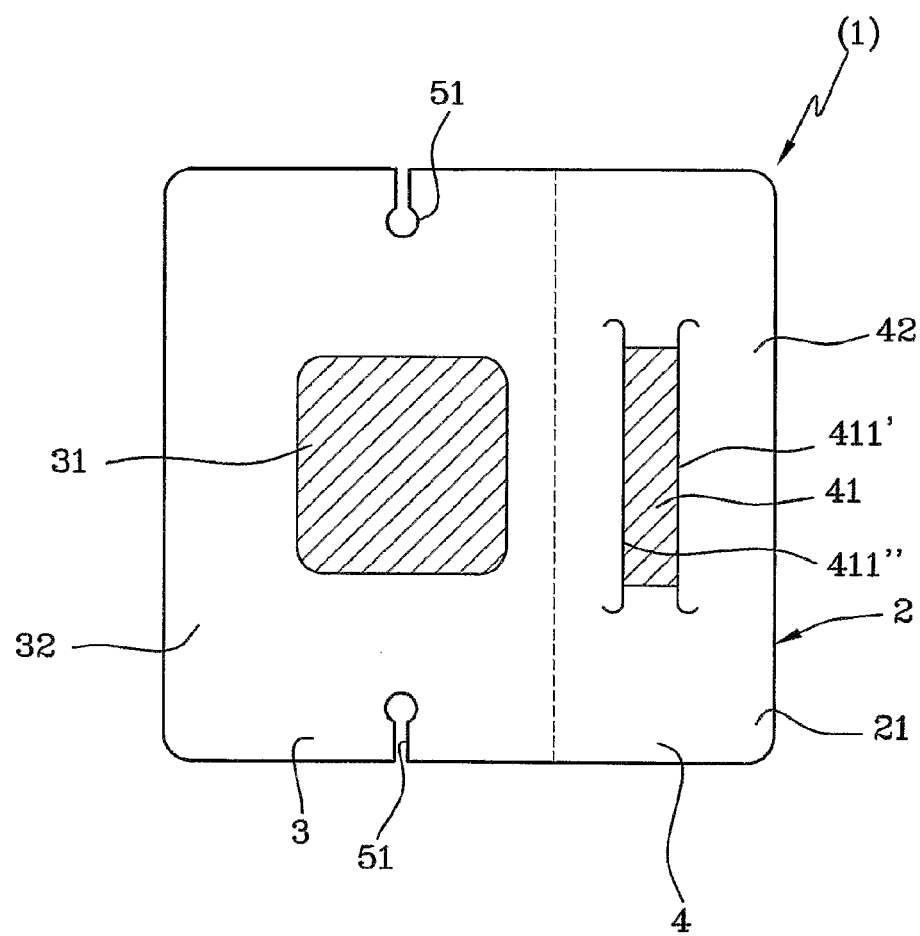
FIG. 1 shows the lower face (the face designed to be turned to the skin) of the bandage, ready to be applied to the patient.
Figure 2:
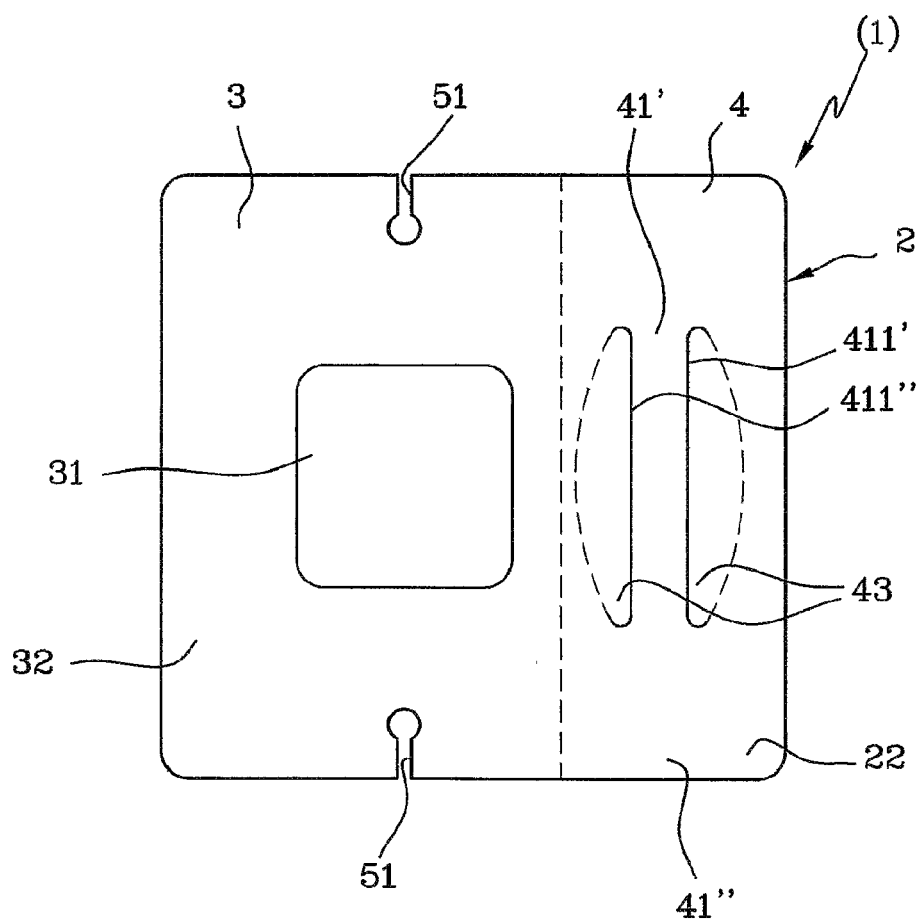
FIG. 2 shows the upper face of the bandage.

The medical-use bandage 1 comprises a lower face designed to be turned to the skin, shown in FIG. 1, and an upper face on the opposite side, shown in FIG. 2.

Figure 4:
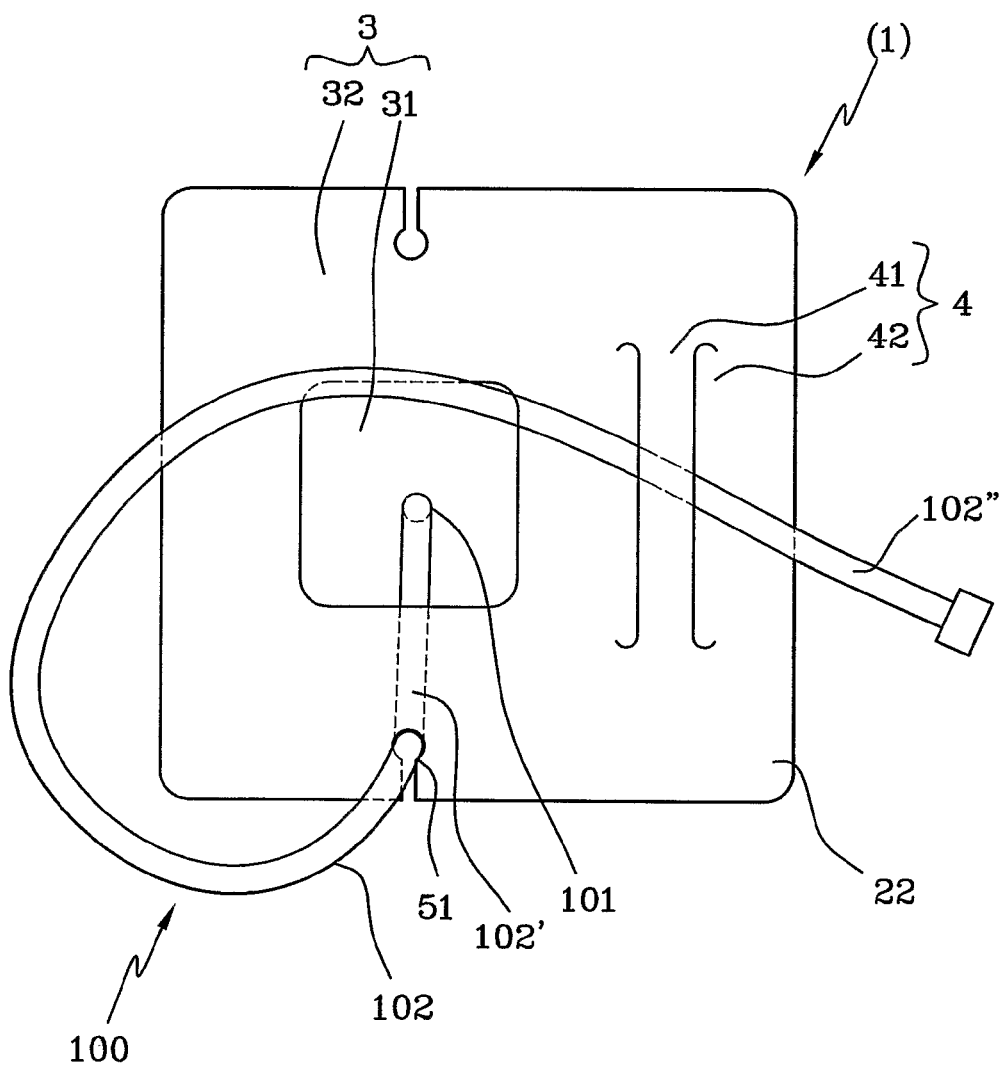
FIG. 4 shows the upper face of the bandage, once the bandage has been applied to the skin, with the projecting portion of the tube immobilized for treatment purposes.

As illustrated in FIG. 4, the bandage is designed to immobilize a tube 100 implanted in a body, the implanted tube 100 defining an exit site 101 from the body and a part 102 of the tube projecting from the body. The projecting part 102 of the tube is composed of a proximal portion 102', that is to say the portion of the tube which is nearest the body and which will be held in place by the first fixing means of the bandage, and a distal portion, that is to say the portion of the tube furthest from the body, a part of which will be held in place during non-treatment by the second fixing means of the bandage in a predetermined shape, preferably a loop.

The bandage 1 comprises a base support 2 having a lower face 21 designed to be applied to the skin. This support may be for example a sheet of an impermeable material, the face applied to the skin consisting of a hypoallergenic material. The material may have good breatheability. All this allows the patient to tolerate the same bandage for several days. The bandage may be coated with a quantity of acrylic adhesive recognized for its high cutaneous tolerance. The material may be made impermeable to bacteria. This material may comprise a natural material such as cotton, woven or otherwise, applied to the lower face of an impermeable sheet, and/or may comprise a polyurethane material. The material may be elastic or rigid. The bandage will be white or flesh-coloured in particular.

The bandage 1 essentially comprises two fixing means for fixing the tube of the catheter at two locations.

The first fixing means 3 for fixing the exit site 101 have on the lower face 21 of the base support 2 an adhesive fixing part 32 designed to be stuck at least partly around the exit site 101 to the skin and to a proximal portion 102' of the projecting part 102 of the tube. The adhesive fixing part 32 (the unhatched area of the first means 3 in FIG. 1) may partly or completely surround the exit site, may be in the shape of a ring on the base support, and may also be made adhesive as far as the edge of the base support. This part may be essentially square as shown in FIG. 1 or rectangular or indeed round.

These first fixing means therefore make it possible to fix the proximal part of the tube of the catheter adhesively and permanently. This means that the proximal part of the tube is fixed adhesively and permanently throughout the period of usage and application of the bandage on the patient (some 2 to 3 days).

The bandage 1 has second fixing means 4 for engaging the distal portion 102" of the projecting part 102 of the tube in a defined shape and in particular in a sliding manner.

More particularly, the second fixing means 4 may comprise:
- a band 41 having at least part of its nonadhesive lower face (the nonadhesive area, shown hatched) designed to be turned to the skin. This band may comprise:
  - two opposite sides (41', 41") connected to the base support 2, and
  - two auxiliary opposite sides (411', 411") defining through the upper face of the bandage 1 two openings for allowing the distal projecting portion 102" of the tube to pass through the openings. The tube can therefore pass between the lower face of the band and the base support, or between the lower face of the band and the skin.

This band is an illustrative embodiment of means allowing the sliding passage of the tube which is to be fixed in position. The band will have all or part of its lower face nonadhesive. The band may be rectangular or square or be of some other shape.

The second fixing means also comprise an adhesive attachment area 42 (the unhatched area) that is situated at least partly around the band 41, is defined on the lower face 21 of the support, and is designed to be stuck to the skin. This attachment area 42 allows the band to be fixed permanently to the skin. The adhesive attachment may surround the band completely or partially.

These second fixing means therefore make it possible to fix nonadhesively and movably, for example in a sliding manner, the distal part of the looped catheter tube. For the entire period of use and application of the bandage on the patient (some 2 to 3 days), the user can thus easily alternate the two positions of the distal part of the tube which correspond to the peritoneal dialysis treatments which he or she has to perform 4 to 5 times every day.

Thus, the tube will be fixed to the second fixing means to form a loop during non-treatment time, and will be withdrawn from the second fixing means during treatment.

If the dressing is left stuck in position for three days and the patient undergoes 5 treatments of peritoneal dialysis per day, this bandage easily allows the tube to be passed underneath the band 3×5=15 times to give it the desired loop position during each of the 15 dialysis treatments. Although the distal part of the tube can be moved (typically by sliding it) because of the second fixing means, the proximal part of the tube will remain adhesively fixed in position by the first fixing means.

Any other embodiment of the second fixing means that may be devised by those skilled in the art may be produced. For example, the fixing band of the second means may be attached by one or both of its sides by means of a fixed or removable attachment to the support, e.g. to facilitate the insertion of the tube through the second fixing means.

The looped position of the tube is wanted during non-treatment time because it has been found by the applicant that this shape ensures that no tension is applied to the point where the catheter emerges due to the weight and length of the external line of the catheter. The external part of the catheter and the extender are thus held securely against the body of the patient and will not move during non-treatment time.

The second fixing means will therefore be situated at a suitable distance from the first fixing means to allow a loop to be formed without too much risk of the tube being creased between the two fixing means. The distance between the two means depends on the dimension of each of the fixing means and/or on the length of external line to be attached.

Without implying any restriction, an example would be a rectangular bandage measuring approximately 10 cm by approximately 9 cm. The window of the first means (the nonadhesive part is transparent or semi-transparent in this example) would be roughly square with sides of approximately 4 cm. The band would be roughly a rectangle with a width of approximately 1 cm and a length of approximately 5 cm. The long sides of the rectangle would be parallel to one side of the square of the window and separated by approximately 2 cm.

The band 41 may essentially be in the shape of a rectangle whose two long sides are the sides defining the two openings (411', 411"). The two long sides have a length greater than the diameter of the tube, sufficient to allow the tube and the connector joining the catheter to the extender to be passed through (the dimension of the extender is greater than the diameter of the tube). This length may be at least twice as great as the dimension of the connector. The two short sides of the rectangle may have a length of for example at least twice the diameter of the tube.

The band 41 can be formed in the base support 2: the two auxiliary sides (411', 411") forming the two openings are produced by two slits made through the thickness of the base support 2. If the band is rectangular, the two long sides of the band are the two slits. The tube will thus be able to be positioned (typically by sliding it) between the lower face of the band and the skin.

Alternatively, the band 41 is a separate element from the base support 2 and is attached to the base support 2 by the opposite sides (41', 41") permanently or removably. In a simple embodiment of this form, the base support of the second fixing means 4 is a sheet and the band is a separate rectangular (for example) sheet attached to the support by two opposite sides. The tube can thus pass, typically by sliding, between the lower face of the band and that part of the upper face of the base support which is next to the band.

The ends of each slit (411', 411") can be formed essentially into an arc of a circle tangent to the auxiliary opposite side and extending away from the band. The diameter of this arc of a circle is small compared with the length of the slit. The arc of a circle may be a semicircle. This form of arc of a circle allows the band to be lifted more easily and gives the band better resistance to movement of the tube. This reduces the risk of the end of an auxiliary opposite side tearing.

The adhesive attachment area 42 of the second fixing means 4 can be in contact with the two auxiliary opposite sides (411', 411") of the band 41. In other words, the lower face of the part 42 of the second fixing means is adhesive at least on each side and in contact with the band 41, for example at least on the areas 43 of the part 42 that are hatched in FIG. 1. This allows the second means to keep the part 42 from moving and enables the tube to be inserted easily underneath the band 41 without the part 42 moving.

The second fixing means 4 may comprise a thickened area 50 formed on the band 41 compared with the thickness of the base support 2, to enhance the strength of the band, which represents that area of the bandage which is subjected to the greatest tensile force.

The thickened area 50 may extend only over the band 41.

A sheet stuck to the lower face 21 of the base support may form the thickened area 50. This embodiment can be envisaged when the base support used for the second means is a film of generally constant thickness with one face entirely adhesive: it is easy to apply definitively the additional sheet which is intended to form the lower face of the band against the adhesive film.

The thickened area 50 may also extend over the full width of the band 41.

The thickened area 50 may extend over a major part of the length of the band and be situated approximately in the middle of the band, as shown in FIG. 1, to leave the ends of the auxiliary opposite sides with no thickened area. The thickened area preferably extends over approximately 80 to 95% of the band 41. This is to prevent tearing of the arcs of circles.

In addition, the first fixing means 3 of the bandage may comprise, on the lower face of the base support, a protective part 31 designed to be placed over the exit site and surrounded by the adhesive fixing part 32. This protective part may be a film consisting of the base support which will be applied to the tube and the exit site to protect them against being knocked. Alternatively, this protective part may be a special sheet attached to the base support. These protective means may comprise a material designed to come into direct contact with the exit site and capable of absorbing any unwanted body fluid that oozes out of the patient's exit site and/or that is capable of forming a barrier to bacteria. The bandage here therefore has a dressing function on the exit site.

The protective part 31 of the first fixing means 3 may be made of a transparent or semi-transparent material, meaning a material such that the exit site is left visible. In this way the condition of the exit site, which stays underneath the dressing for some 2 to 3 days, can be checked visually.

The protective part 31 of the first fixing means 3 may be nonadhesive. This will allow the bandage to be withdrawn definitively without pulling on the part of the tube just in contact with the exit site and without subjecting the tube (which has been permanently implanted by surgery) to undesired pulling and/or withdrawal. For this purpose the user will detach part of the adhesive part 32, place his finger on roughly the part of the tube coming out of the exit site, and detach the rest of the adhesive part 32 stuck to the tube, thus not pulling on the tube.

Moreover, at least one indentation 51 may be formed in an edge of the adhesive fixing part 32 of the first fixing means 3 of the bandage 1. The dimensions of the indentation are such that the projecting part 102 of the tube passing out of the adhesive fixing part 32 of the first fixing means 3 can be engaged in and held by the indentation 51.

The outline of at least one indentation 51 is preferably in the shape of a mushroom so that the tube can be passed along the stalk of the mushroom and the head of the mushroom can accommodate the tube. The width of the stalk may be practically zero (a slit) or be approximately equal to the diameter of the tube.

Alternatively, the outline of the indentation may be an arc of a circle (for example a semicircle) of diameter approximately equal to the diameter of the tube of the catheter or may be V-shaped or may be a combined shape of a slightly rounded V. The indentation may be any other shape envisaged by those skilled in the art capable of accommodating the tube on an edge of the first fixing means.

At least one indentation may be situated on a straight line parallel to the band. This straight line is preferably in the mid-plane of the protective part (31).

The dressing may have one indentation.

Alternatively, the dressing may have two indentations, one on each of the two opposite sides of the first fixing means of the bandage (FIG. 1). This will allow the user to choose which of the 2 indentations to place the tube in. In use, the bandage will be placed on the patient's abdomen in such a way that the first means are situated next to the second means (if the dressing is rectangular as shown in FIG. 1, then it will be arranged so as to extend horizontally across the abdomen).

The catheter tube can be passed through either of the two indentations, as desired. It has been observed that the projecting proximal part of the tube emerging from the abdomen needs to be positioned vertically to achieve a better flow. It is for this reason that the indentations are positioned on the bandage in such a way as to keep the projecting proximal part of the tube vertical.

For storing the bandage and protecting the adhesive parts (32, 42), the lower face of the base support may be entirely covered with a detachable film 70. This detachable film may contain silicone or any other material that can be stuck to one adhesive face and detached without harming the adhesive properties of the face.

In more detail, the detachable film 70 may be composed of one part or of at least two parts. In the case of a nonadhesive film composed of at least two parts, the film is divided into at least a first film part 71 designed to at least partly cover the first fixing means 3 and a second film part 72 designed to at least partly cover the second fixing means 4.

Figure 3:
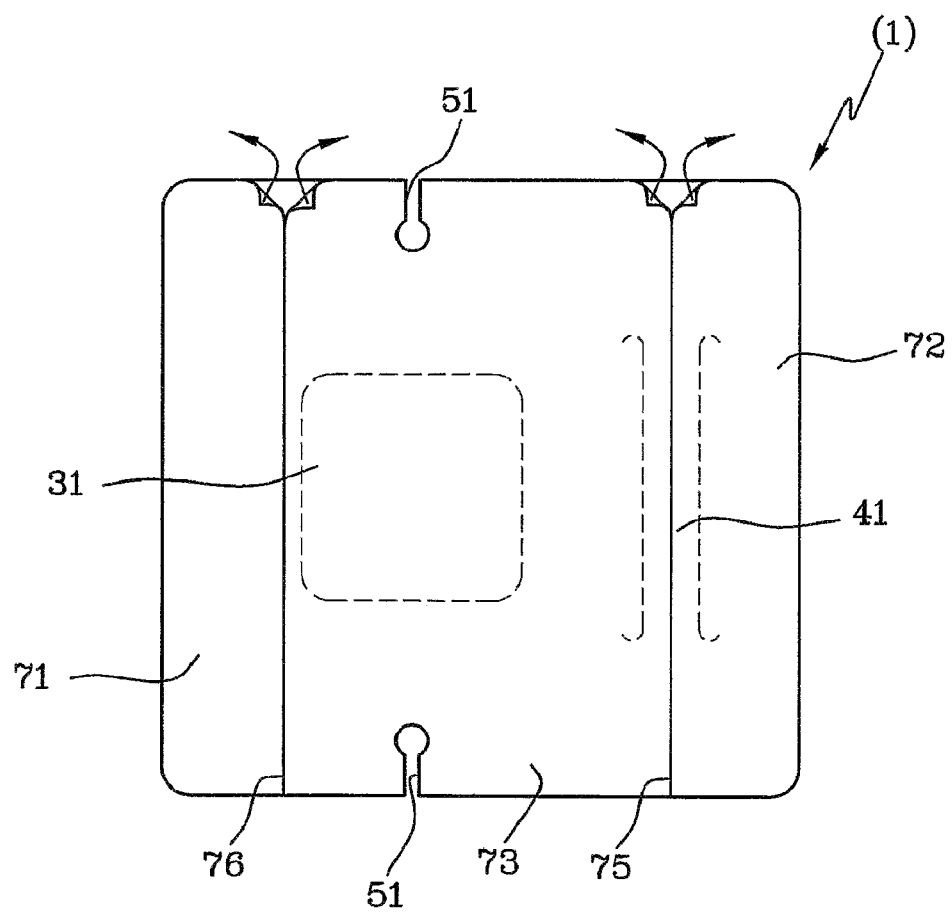
FIG. 3 shows the lower face (the face to be turned to the skin) of the bandage, equipped with detachable films for bandage storage.
Figure 5:
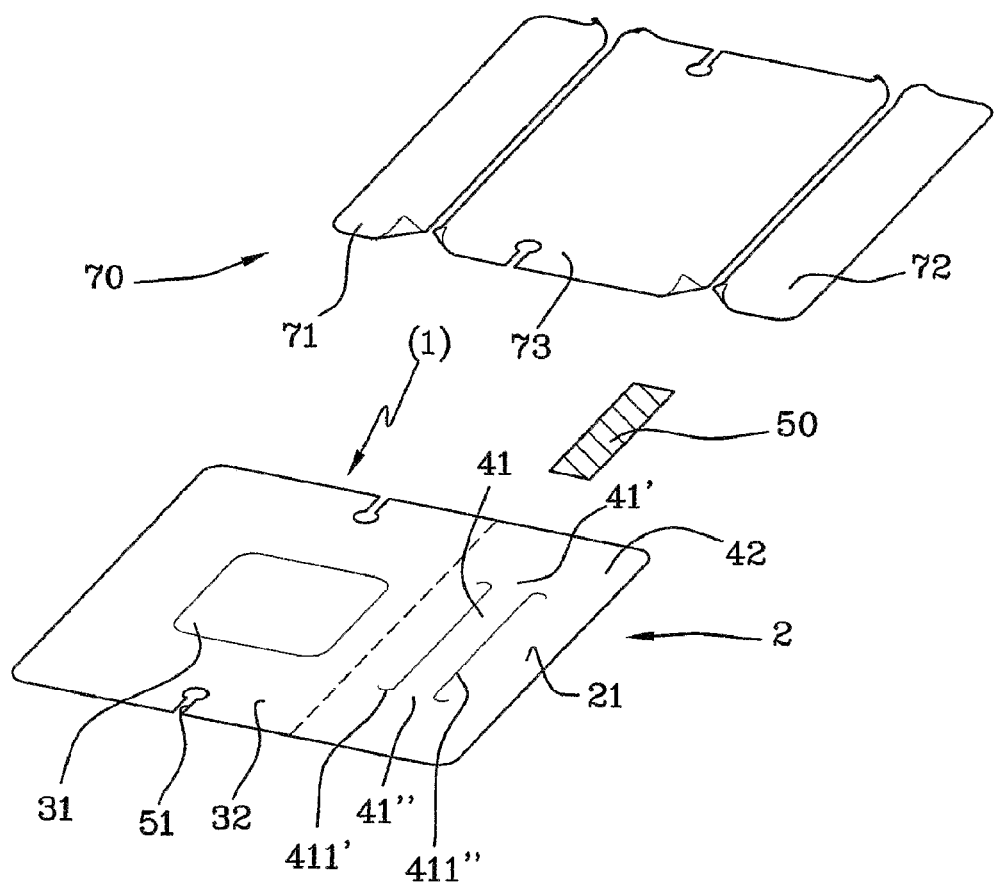
FIG. 5 is an exploded view of the components of the bandage in storage.

More particularly, the detachable film may comprise a third film part 73 designed to cover both a part at least of the first fixing means 3 and a part at least of the second fixing means 4, as illustrated in FIGS. 3 and 5. This will allow the first fixing means to be applied to the skin, followed by the second fixing means, after which the tube can be passed underneath the band.

More particularly, the first film part 71 is designed to cover, about as far as a line 76, a part of the first fixing means 3 that does not include the protective part 31, the second film part 72 is designed to cover a part of the band as far as a line 75 passing between the auxiliary opposite sides (411', 411") of the band 41 of the second fixing means 4, and the third film part 73 intermediate between the first and second film parts (71, 72) is designed to cover the non-covered parts of the first and second fixing means not covered by the first and second film parts (71, 72).

The base support of the bandage can be formed in one piece. In the case of a rectangular bandage, the first fixing means will be roughly a square with sides equal to the width of the rectangle and the second fixing means will be the remaining rectangle, as shown in FIG. 1 by the broken-line boundary. This boundary is purely abstract in the case of a one-piece support, but will be actual in the case of a support made in two pieces composed of the first and second fixing means. That is to say, the base support can be formed in a first part and a separate second part which define the first and second fixing means, respectively.

If the support comprises two pieces, the attachment area 42 of the second fixing means 4 may in one case consist simply of two parts on either side of the band 41 for fixing the band to the skin: the separate second means comprise the band 41, which would be fixed to the skin by at least two opposite adhesive attachment points. In this case, the part 43 of the upper face 22 of the support consists of the upper face of the first fixing means. In another case, the area of attachment 42 of the second fixing means 4 may consist of two parts on either side of the band 41 for fixing the band to the skin and may also consist of the areas 43 shown in FIG. 2 on either side of the auxiliary opposite sides (411', 411"). In this way the area of the second fixing means that adheres to the skin surrounds the band.

The length and/or area of the adhesive attachment points will be decided with respect notably to the length of the nonadhesive base, to prevent either or both points peeling off at the wrong time. For a two-part support, the user selects the optimum spacing between the first and second fixing means so that the loop of the tube can be of the optimum dimensions.

For storage, transport and distribution, the bandage in its packaging has been sterilized, for example with ethylene oxide. The bandage could be sterilized first and then enclosed in its packaging, or the reverse, or the bandage could be sterilized as it is being placed in the unclosed/unsealed packaging. The pack-aging may take the form of a peelable sachet consisting of two faces, e.g. one paper face and one transparent face.

The bandage according to the invention may be envisaged with a medical-use tube fixed to it, the tube having an initial part fixed to the first fixing means, a free intermediate part that is essentially in the form of a loop, and a final part that is fixed in a sliding manner to the second fixing means over at least a part 43 of the upper face 22 of the support 2. The tube/bandage assembly can be applied to the skin of a patient who has an implanted tube, the projecting part of which is to be connected to the tube attached to the bandage.

A process for applying the bandage according to the invention comprises the following steps:
(1) applying and fixing adhesively the first fixing means 3 to the skin and the proximal part of the projecting portion of the tube,
(2) applying and fixing adhesively the second fixing means 4 to the skin, and
(3) forming a loop with the distal portion of the projecting part of the tube and sliding the projecting part of the tube between the lower surface of the band 41 and the skin.

Step (1) may be preceded or followed directly by placing the tube in an indentation 51.

In step (3) the tube is inserted, e.g. slid, between the band and the skin directly, in the case of a band produced by two slits through the base support. Alternatively, in step (3) the tube may be slid between the band and the support directly, in the case of a bandage made of a band added to the base support. In another alternative, step (3) will be total or partial detachment of the support band, positioning of the tube, and re-attachment of the band to place the band over the tube.

The order in which the steps have been written is preferably the order in which the process is carried out in time.

Where the bandage comprises a nonadhesive detachable film 70 comprising a first film part 71 designed to at least partly cover the first fixing means 3, and a second film part 72 designed to at least partly cover the second fixing means 23, the process for applying the bandage will include the following steps:
detaching the first nonadhesive film part 71 from the bandage before the step of fixing adhesively at least in part the first fixing means 3 to the skin and the proximal part of the projecting portion of the tube, and
after fixing the first adhesive means, detaching the second nonadhesive film part 72 from the bandage before the step of fixing adhesively at least in part the second fixing means 4 to the skin.

If the bandage comprises a nonadhesive detachable film 70 divided into a first film part 71 designed to cover a part of the first fixing means 3 which does not include the protective part 31, a second film part 72 designed to cover a part of the band as far as a line 75 passing between the auxiliary opposite sides (411', 411") of the band of the second fixing means 4, and a third film part 73 intermediate between the first and second film parts (71, 72) and designed to cover the non-covered parts of the first and second fixing means not covered by the first and second film parts (71, 72); then the process for applying the bandage includes the following steps:
detaching the third nonadhesive film part 73 from the bandage before the step of fixing adhesively at least the first fixing means 3 to the skin and the proximal part of the projecting portion of the tube and a part of the second fixing means 4 to the skin (this step being preceded or followed directly by passing the tube into an indentation if desired),
detaching the second nonadhesive film part 72 from the bandage before the step of fixing adhesively the other part of the second fixing means 4 to the skin, and
detaching the first nonadhesive film part 71 before the step of fixing adhesively the other part of the first fixing means 3 to the skin.

Advantages of the Invention:

The many advantages of the invention are as follows:
the bandage makes it possible to immobilize the projecting portion of a tube implanted in a patient in a first position during treatment involving the passage of fluid, and immobilizing it in a second position during non-treatment time corresponding to non-passage of fluid,
the bandage is capable of staying in position on the skin for several days,
the bandage provides permanent protection of the patient's exit site,
the bandage permits easy verification of the condition of the exit site throughout the period during which the bandage is on,
the bandage is strong and impermeable to water and/or bacteria,
the bandage is easy and inexpensive to manufacture,
the bandage is easily handled and applied to the skin by the user, and easily detached by the user,
the bandage can be the same colour as the patient's skin colour or white and pass more or less unnoticed,
the bandage saves the nurse or patient time in application,
the bandage is hypoallergenic,
the bandage has good breatheability,
the bandage prevents tugging of the catheter at its point of emergence, and
the bandage is small compared with the length of the external catheter part that is to be fixed.

The invention claimed is:

1. A medical-use bandage for immobilizing a tube implanted in a patient body, with a part of the implanted tube projecting from the body at an exit site, the bandage comprising:
a lower face configured to face skin of the body, and on an opposite side thereof, an upper face;
a base support having the lower face configured to be applied to the skin and the upper face,
a first bandage fixing portion for fixing the exit site, including on the lower face of the base support an adhesive fixing part configured to be adhered at least partly around the exit site to the skin and to a proximal portion of the projecting part of the tube; and
a second bandage fixing portion for (i) engaging the distal portion of the projecting part of the tube in a defined shape and in a sliding manner and (ii) facilitating a complete release of the distal portion of the tube therefrom during a period of patient treatment, the second bandage fixing portion including at least partly a part of the upper face of the base support the second bandage fixing portion including
a band having a nonadhesive lower face, at least part of the nonadhesive lower face being configured to be turned to the skin, the band including
two opposite sides connected to the base support, and two auxiliary opposite sides defining through the upper face of the bandage two openings for allowing the distal portion of the tube to pass through the openings; and an adhesive attachment area that is situated at least partly around the band, is defined on the lower face of the support, and is configured to be adhered to the skin.

2. The bandage according to claim 1, wherein the band is essentially shaped as a rectangle having two long sides that are the sides defining the two openings.

3. The bandage according to claim 1, wherein the band is provided in the base support, and the two auxiliary sides defining the two openings are two slits through a thick dimension of the base support.

4. The bandage according to claim 1, wherein the band is a separate element from the base support and is attached to the base support by the opposite sides.

5. The bandage according to claim 1, wherein ends of each of the auxiliary opposite sides are formed essentially into an arc of a circle tangent to the auxiliary opposite side and extending away from the band.

6. The bandage according to claim 1, wherein the adhesive attachment area of the second bandage fixing portion is in contact with the two auxiliary opposite sides of the band.

7. The bandage according to claim 1, wherein the second bandage fixing portion includes a thickened area on the band relative to a thickness of the base support.

8. The bandage according to claim 7, wherein the thickened area extends only over the band.

9. The bandage according to claim 7, further comprising a sheet adhered to the lower face of the base support, with the sheet forming the thickened area.

10. The bandage according to claim 9, wherein the band is provided in the base support, the two auxiliary sides defining the two openings are two slits through a thick dimension of the base support, and the thickened area extends over a full width of the band.

11. The bandage according to claim 10, wherein the thickened area extends over a major part of the length of the band.

12. The bandage according to claim 1, wherein the first bandage fixing portion includes on the lower face of the base support a protective part configured to be placed over the exit site and surrounded by the adhesive fixing part.

13. The bandage according to claim 12, wherein the protective part is nonadhesive.

14. The bandage according to claim 1, further comprising at least one indentation provided in an edge of the adhesive fixing part of the first bandage fixing portion, the indentation being configured such that the projecting part of the tube passing out of the adhesive fixing part of the first bandage fixing portion can be engaged in and held by the indentation.

15. The bandage according to claim 14, wherein an outline of the at least one indentation has a mushroom shape including a stalk and a head to enable the tube to be passed along the stalk of the mushroom shape and the head of the mushroom shape to accommodate the tube.

16. The bandage according to claim 14, wherein the at least one indentation is situated on a straight line parallel to the band.

17. The bandage according to claim 1, wherein the lower face of the base support is entirely covered with a detachable film.

18. The bandage according to claim 17, wherein the detachable film is nonadhesive and is divided into at least
a first film part configured to at least partly cover the first bandage fixing portion, and
a second film part configured to at least partly cover the second bandage fixing portion.

19. The bandage according to claim 18, wherein the detachable film includes a third film part configured to cover both at least a part of the first bandage fixing portion and at least a part of the second bandage fixing portion.

20. The bandage according to claim 19, wherein
the first film part is configured to cover a part of the first bandage fixing portion that does not include a protective part,
the second film part is configured to cover a part of the band as far as a line passing between the auxiliary opposite sides of the band of the second bandage fixing portion, and
the third film part intermediate between the first and second film parts is configured to cover non-covered parts of the first and second bandage fixing portions not covered by the first and second film parts.

21. The bandage according to claim 1, wherein the base support is provided as one piece.

22. The bandage according to claim 1, wherein the base support is provided as a first part and a second part which define, respectively, the first and second bandage fixing portions.

23. The bandage according to claim 1, wherein the bandage is sterilized and enclosed in packaging.

24. The bandage according to claim 1, to which a medical-use tube is fixed, the tube including
an initial part fixed to the first bandage fixing portion, a free intermediate part that is essentially in a loop form, and a final part that is fixed in a sliding manner to the second bandage fixing portion over at least a part of the upper face of the support.

25. A process for applying the bandage according to claim 1, the process comprising the following steps:
applying and fixing adhesively at least in part the first bandage fixing portion to the skin and the proximal part of the projecting portion of the tube,
applying and fixing adhesively at least in part the second bandage fixing portion to the skin, and
forming a loop with the distal portion of the projecting part of the tube and engaging the projecting part of the tube in a sliding manner in the second bandage fixing portion and in contact with at least the part of the upper surface of the base support.

26. The bandage according to claim 16, wherein the straight line is located in a mid-plane of a protective part configured to be placed over the exit site and surrounded by the adhesive fixing part.

* * * * *

UNITED STATES PATENT AND TRADEMARK OFFICE
CERTIFICATE OF CORRECTION

PATENT NO. : 8,663,171 B2  Page 1 of 1
APPLICATION NO. : 12/300410
DATED : March 4, 2014
INVENTOR(S) : Tambourgi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 956 days.

Signed and Sealed this
Twenty-ninth Day of September, 2015

Michelle K. Lee
*Director of the United States Patent and Trademark Office*